United States Patent
Kuromiya et al.

(10) Patent No.: US 9,345,651 B2
(45) Date of Patent: May 24, 2016

(54) OIL-IN-WATER EMULSION COMPOSITION AND METHOD FOR PRODUCING THE SAME

(75) Inventors: Tomomi Kuromiya, Matsusaka (JP); Daisuke Suzuki, Yamanashi (JP); Masayoshi Miyamoto, Nishinomiya (JP)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 30 days.

(21) Appl. No.: 13/981,170

(22) PCT Filed: Jan. 24, 2012

(86) PCT No.: PCT/EP2012/051012
§ 371 (c)(1),
(2), (4) Date: Jul. 23, 2013

(87) PCT Pub. No.: WO2012/101102
PCT Pub. Date: Aug. 2, 2012

(65) Prior Publication Data
US 2013/0302391 A1   Nov. 14, 2013

(30) Foreign Application Priority Data
Jan. 24, 2011 (JP) ................................ 2011-011958

(51) Int. Cl.
*A61K 8/44* (2006.01)
*A61K 8/06* (2006.01)
*A61Q 19/02* (2006.01)

(52) U.S. Cl.
CPC . *A61K 8/44* (2013.01); *A61K 8/062* (2013.01); *A61Q 19/02* (2013.01); *A61K 2800/21* (2013.01)

(58) Field of Classification Search
CPC ..... A61K 8/44; A61K 2800/21; A61K 8/062; A61Q 19/02
See application file for complete search history.

(56) References Cited

U.S. PATENT DOCUMENTS

| 5,753,241 | A | 5/1998 | Ribier et al. |
| 8,821,905 | B2 * | 9/2014 | Watanabe .................... 424/401 |
| 2002/0155084 | A1 | 10/2002 | Roessler et al. |

FOREIGN PATENT DOCUMENTS

| EP | 0 604 667 A1 | 7/1994 |
| JP | 04-46144 A | 2/1992 |
| JP | 2002-234836 A | 8/2002 |
| JP | 2004-107262 A | 4/2004 |
| JP | 2006-306744 A | 11/2006 |
| JP | 2003/306419 A1 | 6/2011 |
| WO | 00/37071 A1 | 6/2000 |
| WO | 2006/114338 A1 | 11/2006 |
| WO | 2008/050173 A1 | 5/2008 |
| WO | 2009/010356 A1 | 1/2009 |
| WO | 2011/069915 A1 | 6/2011 |
| WO | WO 2011/076207 | * 6/2011 |

OTHER PUBLICATIONS

International Search Report, dated Mar. 7, 2013, from corresponding PCT application.
Okamoto et al., "Development of novel O/W emulsion formulations", IFSCC International Congress Proceedings Venezia, 1994, vol. 2, pp. 327-345.

* cited by examiner

*Primary Examiner* — Ali Soroush
*Assistant Examiner* — Genevieve S Alley
(74) *Attorney, Agent, or Firm* — Young & Thompson

(57) ABSTRACT

Disclosed is an oil-in-water type emulsion composition containing a physiologically acceptable salt of a tranexamate ester and a method for producing the same. An oil-in-water type emulsion composition containing a physiologically acceptable salt of a tranexamate ester can be obtained by preparing an oil phase including: A) a physiologically acceptable salt of a tranexamate ester; B) an amphiphilic substance; C) an oily substance; and D) water, a water-soluble organic solvent or a mixture thereof wherein the weight ratio of the ingredients A:B is in the range of 1:0.5 to 1:2.5, the weight ratio of the ingredients A:C is in the range of 1:1 to 1:5.0, and the weight ratio of the ingredients A:D is 1:0.2 to 1:5.0, and adding the oil phase to a water phase including E) water, a water-soluble organic solvent or a mixture thereof.

18 Claims, 1 Drawing Sheet

|  | Comparative Example 5 | Example 3 |
|---|---|---|
| Appearance after left at room temperature overnight after preparation | Like white milky lotion | Semitransparent |
| Appearance photograph |  |  |
| Particle size distribution (median particle size, μm) | 37 | 0.043 |

OIL-IN-WATER EMULSION COMPOSITION AND METHOD FOR PRODUCING THE SAME

TECHNICAL FIELD

The present invention relates to an oil-in-water emulsion composition comprising a physiologically acceptable salt of a tranexamate ester and a method for producing the same. In addition, the present invention relates to the cosmetic use of the composition and to a cosmetic method for inhibiting skin pigmentation and/or for whitening the skin.

BACKGROUND ART

When a composition for external use such as a drug, a quasi-drug or a cosmetic product is applied to the skin or hair, it is required that the composition fits to the skin or hair with a fresh and refreshing feeling of use, which is characteristic of aqueous cosmetic materials such as a skin lotion or gel-like cosmetic materials. Besides, after application, it is required that the composition imparts wet moisture to the skin or hair with a smooth and soft feeling of use, which is characteristic of cosmetic materials containing an oily ingredient such as a cream or a milky lotion.

However, it is generally difficult to disperse oily ingredients and aqueous ingredients in a stable form together for a long term; thus it is difficult to achieve a fresh and refreshing feeling of use after having combined an oily ingredient with an aqueous cosmetic material, which can be used as a cream, a milky lotion or the like.

Emulsification is known as a technology for dispersing oily ingredients in an aqueous medium. In recent years, the emulsification technology has been evolving, and interest has been attracted to the creation of a new effect and feeling of use by emulsification. For example, it is expected to achieve a feeling of use free from an icky feeling of an oily ingredient by dispersing the oily ingredient in an aqueous composition in the form of fine emulsification particles. Attempts have been made to disperse an oily ingredient by converting it to fine emulsification particles under high shearing force in an aqueous medium (Okamoto T., et al., The 18th IFSCC international congress proceedings, Venezia, vol. 2, 327 (1994) (Non-Patent Document 1)). However, this method requires a special device to achieve the high shearing force.

Meanwhile, a whitening effect of a tranexamate ester has been known, and the same has been used as a whitening ingredient in compositions for external use. For example, Japanese Patent Laid-Open No. 04-46144 (Patent Document 1) describes an anti-pigmentation agent for external use using a tranexamate ester as an active ingredient.

Japanese Patent Laid-Open No. 2003-306419 (Patent Document 2) exemplifies tranexamic acid and derivatives thereof as whitening ingredients to be usable with coenzyme Q10. Japanese Patent Laid-Open No. 2004-107262 (Patent Document 3) exemplifies a cetyl tranexamate ester as an oil-soluble whitening agent to be usable with an L-ascorbic acid tetra-branched fatty acid ester derivative.

However, a problem of a tranexamate ester or a salt thereof is that it is sparingly soluble in water and oil and this is likely to cause aggregates in a formulation, and thus it is difficult to incorporate it in a formulation in a stable state.

For example, Japanese Patent Laid-Open No. 2002-234836 (Patent Document 4) describes an anti-stress composition for external use using a tranexamate ester as an active ingredient. It also describes dissolution of a tranexamate ester using a large amount of an oily ingredient such as olive oil. However, by this method, the formulation form is limited to a cream or a milky lotion due to the use of a large amount of an oily ingredient. Additionally, the obtained agent for external use is sticky and oily and the feeling of use is unfavorable.

Further, Japanese Patent Laid-Open No. 2006-306744 (Patent Document 5) describes a composition for external use using a tranexamate ester or a salt thereof as well as a silicone oil. It also states that by the combination of a tranexamate ester or a salt thereof and a silicone oil the solubility of the tranexamate ester or the salt thereof in the composition can be enhanced, and the effect of the tranexamate ester can last over an extended time period. Silicone oil is known as an oily ingredient giving a relatively refreshing feeling of use, but it is necessary to use a large amount thereof for dissolving a tranexamate ester, and such a fresh and refreshing feeling of use as given by aqueous cosmetic materials cannot be obtained.

CITATION LIST

[Patent Document]
[Patent Document 1] Japanese Patent Laid-Open No. 04
[Patent Document 2] Japanese Patent Laid-Open No. 2003-306419
[Patent Document 3] Japanese Patent Laid-Open No. 2004-107262
[Patent Document 4] Japanese Patent Laid-Open No. 2002-234836
[Patent Document 5] Japanese Patent Laid-Open No. 2006-306744
[Non-Patent Document]
[Non-Patent Document 1] Okamoto T., et al., The 18$^{th}$ IFSCC international congress proceedings, Venezia, vol. 2, 327 (1994)

SUMMARY OF INVENTION

Problems to be Solved by the Invention

Under these circumstances, there is still a need for a composition for external use fitting to the skin or hair with a fresh and refreshing feeling of use when applied to the skin or hair, as well as imparting wet moisture to the skin or hair with a smooth and soft feeling of use after application. In addition, a method for incorporating a tranexamate ester or a salt thereof in a stable form in a composition for external use is demanded. It is desirable that the above mentioned composition for external use be produced by a simple and easy method without needing a special device.

Means for Solving the Problems

The present inventors have conducted intensive studies to solve the above mentioned problem. They consequently have found that when a physiologically acceptable salt of a tranexamate ester, an amphiphilic substance and an oily substance, at a specific quantitative ratio, are mixed in an aqueous medium by an ordinary mixing operation, a composition having a semitransparent appearance, in which the oily substance is dispersed in the form of fine emulsified particles in the aqueous medium, is obtained.

The feeling of use of an aqueous cosmetic material, and the feeling of use of a cosmetic material in which an oily ingredient is incorporated, are obtained when an oily ingredient is dispersed in the form of fine emulsified particles in an aqueous medium. Furthermore, this method enables a physiologically acceptable salt of a tranexamate ester to be dispersed in a stable form. Therefore, the obtained composition can have a whitening effect on the skin and the like. Such a composition can be used as a composition for external use of drugs, quasi-drugs and cosmetic products.

The present inventors have considered that the reason why fine emulsified particles can be obtained by an ordinary mixing operation, without using a special device, is because the interfacial tension between the oily substance and the aqueous medium is remarkably decreased by the physiologically acceptable salt of a tranexamate ester and the amphiphilic substance. As a result of having intensively examined the conditions under which fine emulsification particles can be formed based on that consideration, the inventors have reached the present invention.

That is, the present invention relates to an oil-in-water emulsion composition and a method for producing the same. In addition, the present invention relates to the cosmetic use of the composition and to a cosmetic method for inhibiting skin pigmentation and/or for whitening the skin. Furthermore, the present invention relates to the emulsified particles as obtained by the production method.

Thus, the present invention relates to an oil-in-water emulsion composition comprising:
A) a physiologically acceptable salt of a tranexamate ester,
B) an amphiphilic substance, and
C) an oily substance,
wherein a weight ratio of the ingredients A:B is in the range of 1:0.5 to 1:2.5 and a weight ratio of the ingredients A:C is in the range of 1:1 to 1:5.0. The tranexamate ester is preferably represented by the following formula (1):

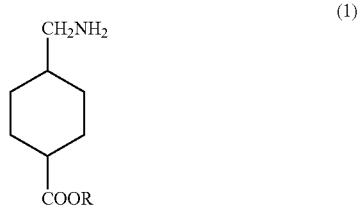

wherein R represents a linear or branched, saturated or unsaturated hydrocarbon group having 1 to 22 carbon atoms, which may be substituted by a substituent selected from a hydroxyl group and an amino group.

Preferably, the physiologically acceptable salt of a tranexamate ester is cetyl tranexamate hydrochloride. Preferably, the amphiphilic substance is selected from a group consisting of alcohols, fatty acids, fatty acid esters, fatty acid ethers, glycerin fatty acid esters and glycerin monoalkyl ethers which have a carbon chain length of 6 to 22.

Preferably, the carbon chain length of the amphiphilic substance is 12 to 22.

Preferably, the carbon chain length of the physiologically acceptable salt of a tranexamate ester is 12 to 18 and the carbon chain length of the amphiphilic substance is 12 to 22.

Preferably the average particle size (median diameter) of the emulsified particles is 12 nm to 100 nm.

The present invention relates to a method for producing an oil-in-water emulsion composition, comprising the following steps:
a step of preparing an oil phase comprising:
  A) a physiologically acceptable salt of a tranexamate ester,
  B) an amphiphilic substance,
  C) an oily substance and
  D) water, a water-soluble organic solvent or a mixture thereof,
wherein a weight ratio of the ingredients A:B is in the range of 1:0.5 to 1:2.5, a weight ratio of the ingredients A:C is in the range of 1:1 to 1:5.0 and a weight ratio of the ingredients A:D is 1:0.2 to 1:5.0; and adding the oil phase to a water phase comprising
  E) water, a water-soluble organic solvent or a mixture thereof.

In the method according to the invention, the weight ratio of oil phase: water phase is preferably in the range of 1:1 to 30.

Preferably, the oil phase and the aqueous phase are respectively maintained at 75° C. and 95° C. before adding said oil phase to said aqueous phase.

The present invention also covers the cosmetic use of the composition according to the invention for inhibiting skin pigmentation and/or for whitening the skin, and/or to reduce aging spots or pigmentation spots. The present invention also relates to a cosmetic method for inhibiting skin pigmentation and/or for whitening the skin, comprising the topical application of the composition according to the invention to the skin. The present invention also relates to the emulsified particles obtained by the method according to the invention, which have an average particle size (median diameter) of 12 nm to 100 nm.

Advantages of Invention

According to a preferable aspect of the present invention, the composition according to the invention has both the feeling of use of an aqueous cosmetic material and the feeling of use of a cosmetic material containing an oily ingredient. In addition, according to a preferable aspect of the present invention, a physiologically acceptable salt of a tranexamate ester exhibiting a whitening effect can be formulated in a stable form.

BRIEF DESCRIPTION OF THE DRAWINGS

FIG. 1 compares the appearance of the compositions of Example 3 and Comparative Example 5, checked by visual observation, the appearance photographs taken with a digital camera and the measured values of particle size distribution.

MODES FOR CARRYING OUT THE INVENTION

In the following, the oil-in-water emulsion composition, the method for producing the same and the use of the composition according to the present invention will be described in detail.

The oil-in-water emulsion composition of the present invention comprises:
A) a physiologically acceptable salt of a tranexamate ester,
B) an amphiphilic substance, and
C) an oily substance,
wherein a weight ratio of the ingredients A:B is in the range of 1:0.5 to 1:2.5 and a weight ratio of the ingredients A:C is in the range of 1:1 to 1:5.0.

As described above, A) a physiologically acceptable salt of a tranexamate ester (hereinbelow also referred to as "tranexamate ester salt"); B) an amphiphilic substance; and C) an oily substance, are used at a specific weight ratio in the oil-in-water emulsion composition of the present invention. Fine emulsified particles can be formed in an aqueous medium by using the ingredients A, B and C mentioned above at this weight ratio.

Tranexamate Ester Salt

Preferably the tranexamate ester in the present invention is represented by the following formula (1):

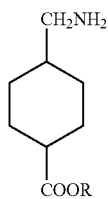

(1)

wherein R represents a linear or branched, saturated or unsaturated hydrocarbon group having 1 to 22 carbon atoms, which may be substituted by a substituent selected from a hydroxyl group and an amino group.

In Formula (1), R represents a linear or branched, saturated or unsaturated hydrocarbon group having 1 to 22 carbon atoms, in which a hydrogen atom contained therein may be replaced by a substituent selected from a hydroxyl group and an amino group.

The hydrocarbon group may be acyclic or cyclic. In the case where the hydrocarbon group is acyclic, it may be a linear or branched chain. Examples of the hydrocarbon group includes: an alkyl group, an alkenyl group, an alkynyl group, an alkyldienyl group, an aryl group, an alkylaryl group, an arylalkyl group, a cycloalkyl group, a cycloalkenyl group and a cycloalkylalkyl group. Among them an alkyl group is preferable. The number of carbon atoms is preferably 8 to 20, and especially preferably 12 to 18.

There are no particular restrictions on the number of substituents on the hydrocarbon group. In the case where the hydrocarbon group has 2 or more substituents, the substituents may be either hydroxyl groups or amino groups, or both of hydroxyl group(s) and amino group(s).

Specific examples of the tranexamate ester represented by Formula (1) include lauryl tranexamate, myristyl tranexamate, cetyl tranexamate and stearyl tranexamate. Among them, cetyl tranexamate is especially preferable.

There are no particular restrictions on the physiologically acceptable tranexamate ester salt to be used in the present invention, as long as the object of the present invention is not impeded. Preferred examples of the tranexamate ester salt to be used in the present invention include a mineral acid salt, such as hydrochloride, phosphate, sulfate, bromate, and nitrate; an organic acid salt, such as oxalate, lactate, and citrate; and carbonate of a tranexamate ester.

Among others a tranexamate ester salt to be used in the present invention is preferably selected from the group consisting of cetyl tranexamate hydrochloride, cetyl tranexamate phosphate, cetyl tranexamate sulfate, cetyl tranexamate bromate, cetyl tranexamate nitrate, cetyl tranexamate oxalate, cetyl tranexamate lactate, cetyl tranexamate citrate, cetyl tranexamate carbonate and their mixtures. Cetyl tranexamate hydrochloride is especially preferable.

Amphiphilic Substance

The amphiphilic substance for use in the present invention is not particularly limited as long as the substance is a substance having a hydrophilic group and a hydrophobic group. Examples of amphiphilic substances for use in the present invention preferably include those commonly used in compositions for external use. Specifically, higher alcohols, higher fatty acids, fatty acid esters, fatty acid ethers, glycerin fatty acid esters and glycerin monoalkyl ethers, etc. which have a 6 to 22 carbon chain length, preferably a 12 to 22 carbon chain length, can be included. Among these, higher alcohols are preferable as the amphiphilic substances. In particular, higher alcohols which have a 6 to 22 carbon chain length, preferably a 12 to 22 carbon chain length, are preferable.

Examples of the higher alcohol include linear alcohols, such as lauryl alcohol, cetyl alcohol, stearyl alcohol, behenyl alcohol, myristyl alcohol, oleyl alcohol, and cetostearyl alcohol; and branched alcohols, such as 2-decyltetradecanol, lanolin alcohol, cholesterol, phytosterol, hexyldodecanol, isostearyl alcohol, and octyldodecanol. Among them, linear alcohols are preferable.

Examples of the higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

Examples of the fatty acid ethers include polyoxyethylene fatty acid ethers and polyoxypropylene fatty acid ethers.

Examples of the fatty acid esters include polyoxyethylene fatty acid esters, polyoxyethylene sorbitan fatty acid esters, polyoxyethylene sorbit fatty acid esters and sucrose fatty acid esters.

Examples of the glycerin fatty acid esters include glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate.

Examples of the glycerin monoalkyl ethers include chimyl alcohol (glycerin monocetyl ether), selachyl alcohol (glycerin monooleyl ether), batyl alcohol (glycerin monostearyl ether).

The amphiphilic substance may be used as a single agent or in combination.

Oily Substance

The oily substance for use in the present invention is a material having a property of not dissolving or being difficult to dissolve in water and being easy to dissolve in oil. Examples of the oily substance for use in the present invention preferably include low viscosity liquid oils/fats, solid oils/fats, waxes, hydrocarbon oils, synthetic ester oils, silicone oils and silicone elastomers that are commonly used in compositions for external use.

Examples of the liquid oil/fat (oil/fat which is liquid at room temperature (25° C.)) include avocado oil, camellia oil, turtle oil, macadamia nut oil, corn oil, mink oil, olive oil, rapeseed oil, yolk oil, sesame oil, persic oil, wheat germ oil, camellia kissi oil, castor oil, linseed oil, safflower oil, cotton seed oil, perilla oil, soybean oil, peanut oil, tea seed oil, Torreya seed oil, rice bran oil, Chinese tung oil, Japanese tung oil, jojoba oil, germ oil, and triglycerin.

Examples of the solid oil/fat (oil/fat which is solid at room temperature (25° C.)) include cacao butter, coconut oil, horse tallow, hardened coconut oil, palm oil, palm kernel oil, Japan tallow kernel oil, hardened oil, Japan tallow, and hardened castor oil.

Examples of the wax include bees wax, candelilla wax, cotton wax, carnauba wax, bayberry wax, Chinese insect wax, montan wax, bran wax, lanolin, kapok wax, acetylated lanolin, liquid lanolin, sugar cane wax, lanolin fatty acid isopropyl ester, hexyl laurate, reduction lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of the hydrocarbon oil include liquid paraffin, ozokerite, squalane, pristane, paraffin, ceresin, squalene, vaseline, microcrystalline wax, hydrogenated polydecene, and isododecane.

Examples of the synthetic ester oil include tripropylene glycol dineopentanoate, isononyl isononanoate, isotridecyl isononanoate, isopropyl myristate, cetyl octanoate, cetyl isooctanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprylate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, bis-behenyl/isostearyl/phytosteryl dimer dilinoleyl dimer dilinoleate, phytosteryl/behenyl/octyldodecyl/isostearyl lauroyl glutamate, tri(caprylic acid/capric acid) glyceryl, and triethylhexanoin.

Examples of the silicone oil include a polysiloxane chain, such as dimethicone (dimethylpolysiloxane), methyl trimethicone, methylphenylpolysiloxane and diphenylpolysiloxane; a cyclic polysiloxane, such as octamethyl cyclotetrasiloxane, decamethyl cyclopentasiloxane and dodecamethyl cyclohexasiloxane; a silicone resin forming a 3D net structure; a silicone rubber; and various modified polysiloxanes, such as amino-modified polysiloxane, polyether-modified polysiloxane, alkyl-modified polysiloxane and fluorine-modified polysiloxane.

Examples of silicone elastomers include non-emulsifying organopolysiloxane elastomers and emulsifying organosiloxane elastomers. Examples of the non-emulsifying organopolysiloxane elastomers include dimethicone/vinyl dimethicone crosspolymers and lauryl dimethicone/vinyl dimethicone crosspolymers.

The dimethicone/vinyl dimethicone crosspolymers include products commercially available from DOW CORNING (Midland, Mich.) under the trade names of, for example, DC 9040 and DC 9045; products commercially available from MOMENTIVE under the trade name of SFE 839 and the Velvasil series products; products commercially available from Shin-Etsu Chemical Co., Ltd. under the trade names of, for example, KSG-15, KSG-16, and KSG-18 ([dimethicone/phenyl vinyl dimethicone crosspolymer]); and Gransil™ series products from GRANT INDUSTRIES, Inc.

The lauryl dimethicone/vinyl dimethicone crosspolymers include products commercially available from Shin-Etsu Chemical Co., Ltd. under the trade names of, for example, KSG-31, KSG-32, KSG-41, KSG-42, KSG-43, and KSG-44.

Examples of the emulsifying organosiloxane elastomers include polyalkoxylated silicone elastomers and polyglycerolated silicone elastomers.

The polyalkoxylated silicone elastomers include products commercially available from DOW CORNING under the trade names of, for example, DC9010 and DC9011; and products commercially available from Shin-Etsu Chemical Co., Ltd. under the trade names of, for example, KSG-20, KSG-21, KSG-30, KSG-31, KSG-32, KSG-33, KSG-210, KSG-310, KSG-320, KSG-330, KSG-340, and X-226146.

The polyglycerolated silicone elastomers include products commercially available from Shin-Etsu Chemical Co., Ltd. under the trade names of, for example, KSG-710, KSG-810, KSG-820, KSG-830, KSG-840, KSG-31, KSG-32, KSG-41, KSG-42, KSG-43, and KSG-44. In addition, examples of silicone elastomers into which 2 types of branches, i.e. a silicone chain and an alkyl chain, have been introduced, include products commercially available from Shin-Etsu Chemical Co., Ltd. under the trade names of, for example, KSG-042Z, KSG-045Z, KSG-320Z, KSG-350Z, KSG-820Z, and KSG-850Z.

Silicone elastomers comprising a polyalkyl ether group as pendant or cross-linked may also be used. Particularly suitable silicone elastomers comprising a polyalkyl ether group include compounds with an INCI name of bis-vinyldimethicone/bis-isobutyl PPG-20 crosspolymer, bis-vinyldimethicone/PPG-20 crosspolymer, dimethicone/bis-isobutyl PPG-20 crosspolymer, dimethicone/PPG-20 crosspolymer, and dimethicone/bis-secbutyl PPG-20 crosspolymer. Such crosslinked elastomers are available from Dow Corning under the experimental compound names of SOEB-1, SOEB-2, SOEB-3 and SOEB-4, and under the proposed commercial name of DC EL-8052 IH Si Organic Elastomer Blend. The elastomer particles are supplied pre-swollen in the respective solvents, isododecane (for SOEB-1 and -2), isohexadecane (for SOEB-3) and isodecyl neopentanoate (for SOEB-4).

These oils may be used singly or in combination of two or more of them.

In the oil-in-water type emulsion composition of the present invention, the quantitative ratio of the ingredient A (tranexamate ester salt), the ingredient B (amphiphilic substance) and the ingredient C (an oily substance) is as shown below. The quantitative ratio of the ingredient A and the ingredient B is ingredient A:ingredient B=1:0.5 to 1:2.5, preferably 1:1.0 to 1:2.0, more preferably 1:1.5 to 1:2.0 by weight ratio. The quantitative ratio of the ingredient A and the ingredient C is ingredient A:ingredient C=1:1 to 1:5.0, preferably 1:2.0 to 1:4.0, more preferably 1:2.5 to 1:3.5 by weight ratio. When the ingredients A, B and C are used in this quantitative ratio, the size of the emulsification particles can be decreased without high shearing with a special device. It is considered that since the size of the emulsified particles can be decreased, the composition can fit to the skin or hair with a fresh and refreshing feeling of use when applied to the skin or hair, as well as can impart wet moisture to the skin or hair with a smooth and soft feeling of use, due to the contained oily ingredient. In addition, as the size of the emulsified particles becomes smaller, more stable oil-in-water emulsion compositions can be obtained.

It is preferable that the carbon chain length of the tranexamate ester salt A) and the carbon chain length of an amphiphilic substance B) be in good balance in order to form more stable emulsified particles. Specifically, it is preferable that the carbon chain length of the tranexamate ester salt A) be 12 to 18 and that the carbon chain length of the amphiphilic substance B) be 12 to 22. Furthermore, it is preferable that the carbon chain length of the tranexamate ester salt A) be 14 to 18 and that the carbon chain length of the amphiphilic substance B) be 14 to 22. It is particularly preferable that the carbon chain length of the tranexamate ester salt A) and the carbon chain length of the amphiphilic substance B) be the same. It is considered that when the carbon chain length of the tranexamate ester salt A) and the carbon chain length of the amphiphilic substance B) are the same, a stable hydrophobic film is formed around the oily ingredient by these carbon chain lengths.

According to a preferable aspect of the present invention, the average particle size of the emulsified particles in the oil-in-water emulsion composition of the present invention is 12 nm to 100 nm, preferably 12 nm to 80 nm, more preferably 12 nm to 60 nm. When the size of the emulsified particles is at a nano level, the oil-in-water emulsion composition of the present invention can have a semitransparent appearance and impart a fresh and refreshing feeling of use closer to that of the aqueous cosmetic ingredient when applied to the skin or hair although the composition contains a specific amount of an oily ingredient. In addition, the average particle size of the emulsified particles in the present invention is a median diameter measured with a laser diffraction particle size distribution measuring apparatus.

It is considered that the reason why fine emulsified particles can be obtained without needing high shearing with a special device in an oil-in-water emulsion composition, is because the tranexamate ester salt, having a hydrophilic group and a lipophilic group in a molecule, functions as a surfactant and lowers surface free energy at the interface between the oily ingredient and the aqueous medium. That is, the present invention conversely makes good use of the property of the tranexamate ester salt indicating that solubility thereof is low for both water and oil. It is considered that this allows not only both the feeling of use of an aqueous cosmetic material and the feeling of use of a cosmetic material containing an oily ingredient, but also a whitening effect due to the tranexamate ester salt to be imparted to the oil-in-water emulsion composition of the present invention, by formulating the tranexamate ester salt in a stable form.

Water, Water-Soluble Organic Solvent or Mixture Thereof.

In the oil-in-water type emulsion composition of the present invention, the emulsified particles mentioned above are dispersed in an aqueous medium including water, a water-soluble organic solvent or a mixture thereof.

The water-soluble organic solvent for use in the present invention is not particularly limited and examples thereof preferably include those commonly used in compositions for external use. Examples thereof include lower alcohols (preferably, alcohols having 1 to 4 carbon atoms) such as methanol, ethanol, propanol, isopropanol; and polyhydric alcohols such as ethyleneglycol, 1,3-butylene glycol, propylene glycol, dipropylene glycol, isoprene glycol, polyethylene glycol, polyoxyethylene methylglucoside, glycerin and diglycerine.

These water-soluble organic solvents can be used singly or in combination of two or more of them.

The content of water, a water-soluble organic solvent or a mixture thereof is not particularly limited. The total of the content of water, a water-soluble organic solvent or a mixture thereof and a water-soluble ingredient is adjusted to the range of preferably 40 to 95% by weight, more preferably 50 to 90% by weight, and particularly preferably 60 to 80% by weight, based on the total weight of the oil-in-water emulsion composition of the present invention. The amount of solvent may vary depending on the use of the oil-in-water emulsion composition. The amount of solvent can be appropriately determined according to the use of the oil-in-water emulsion composition.

Optional Ingredients

The oil-in-water emulsion composition of the present invention can optionally comprise ingredients in addition to the above to such an extent that the ingredients do not impair the object and effects of the present invention. For example, ingredient(s) which can be contained in compositions for external use such as drugs, quasi drugs or cosmetic products can be contained.

As the optional ingredient(s), for example, powder ingredient(s), surfactant(s), cosurfactant(s), moisturizer(s), film agent(s), thickener(s), gelatinizer(s), inorganic mineral(s), sequestering agent(s), polyhydric alcohol(s), monosaccharide(s), oligosaccharide(s), amino acid(s), plant extract(s), organic amine(s), polymer emulsion(s), antioxidant(s), oxidization prevention assistant(s), skin nutritional supplement(s), vitamin(s), bloodstream accelerant(s), sterilizer(s), antiphlogistic (antiinflammation) agent(s), cell (skin) activation agent(s), keratolytic agent(s), tonic(s), astrictive(s), whitening agent(s), UV absorber(s), fading inhibitor(s), preservative(s), pH regulator(s), buffer(s) and/or fragrance(s) can be appropriately contained as needed. These optional ingredients can be appropriately selected depending on the formulation form and use to be aimed.

Examples of the powder ingredients include inorganic powders (for example, talc, kaolin, mica, sericite, muscovite, phlogopite, synthetic mica, deep red mica, biotite, vermiculite, magnesium carbonate, calcium carbonate, aluminum silicate, barium silicate, calcium silicate, magnesium silicate, strontium silicate, tungstic acid metal salt, silica, zeolite, barium sulfate, magnesium sulfate, burnt calcium sulfate (plaster), calcium phosphate, fluorine apatite, hydroxyapatite, ceramic powders, metallic soaps (for example, zinc myristate, calcium palmitate, aluminum stearate, magnesium stearate), boron nitride); organic powders (for example, polyamide resin powder (nylon powder), polyethylene powder, polymethyl methacrylate powder, polystyrene powder, co-polymer resin powder of styrene and acrylic acid, benzoguanamine resin powder, polytetrafluoroethylene powder, cellulose powder); metallic powder pigments (for example, aluminum powder, copper powder), organic pigments such as zirconium, barium or aluminum lakes; and natural pigments (for example, chlorophyll, β-carotene). Here, the powder ingredients may be subjected to a hydrophobic treatment.

The surfactants may include anionic surfactants, cationic surfactants, ampholytic surfactants, lipophilic nonionic surfactants and hydrophilic nonionic surfactants.

Examples of the anionic surfactant include fatty acid soaps (for example, sodium laurate and sodium palmitate); higher alkyl sulfate salts (for example, sodium lauryl sulfate and potassium lauryl sulfate); alkylether sulfate salts (for example, triethanolamine POE-lauryl sulfate and POE-sodium lauryl sulfate); N-acyl sarcosine acids (for example, sodium lauroylsarcosinate); higher fatty acid amide sulfonates (for example, sodium N-myristoyl-N-methyl taurate, sodium cocoyl methyl tauride and sodium lauryl methyltauride); phosphate salts (sodium POE-oleyl ether phosphate, a POE-stearyl ether phosphoric acid, etc.); sulfosuccinates (for example, sodium di-2-ethylhexylsulfosuccinate, sodium monolauroyl monoethanolamide polyoxyethylene sulfosuccinate and sodium lauryl polypropylene glycol sulfosuccinate); alkyl benzenesulfonates (for example, linear sodium dodecylbenzenesulfonate, linear triethanolamine dodecylbenzenesulfate and a linear dodecylbenzenesulfonic acid); higher fatty acid ester sulfate salts (for example, sodium cocomonoglyceride sulfate); N-acyl glutamates (for example, monosodium N-lauroyl glutamate, disodium N-stearoyl glutamate and monosodium N-myristoyl-L-glutamate); sulfated oils (for example, Turkey red oil); POE-alkylether carboxylic acids; POE-alkylarylether carboxylates; α-olefin sulfonates; higher fatty acid ester sulfonates; secondary alcohol sulfate ester salts; higher fatty acid alkylolamide sulfate ester salts; sodium lauroyl monoethanolamide succinates; ditriethanolamine N-palmitoyl aspartate and sodium casein.

Examples of the cationic surfactant include alkyltrimethylammonium salts (for example, stearyltrimethylammonium chloride and lauryltrimethylammonium chloride); alkylpyridinium salts (for example, cetylpyridinium chloride); a chloride distearyldimethylammonium dialkyldimethylammonium salt; poly(N,N'-dimethyl-3,5-methylene piperidium) chloride; alkyl quaternary ammonium salts; alkyldimethylbenzylammonium salts; alkylisoquinolinium salts; dialkylmorpholium salts; POE-alkylamine; alkylamine salts; polyamine fatty acid derivatives; amylalcohol fatty acid derivatives; benzalkonium chloride; and benzethonium chloride.

Examples of the ampholytic surfactant include imidazoline-based ampholytic surfactants (for example, sodium 2-undecyl-N,N,N-(hydroxyethylcarboxymethyl)-2-imidazoline; and a 2-cocoyl-2-imidazolinium hydroxide-1-carboxyethyloxy disodium salt); and betaine-based surfactants (for example, 2-heptadecyl-N-carboxymethyl-N-hydroxyethyl imidazolinium betaine, lauryldimethylamino acetate betaine, alkyl betaine, amide betaine, and sulfobetaine).

Examples of the lipophilic nonionic surfactant include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; glyceryl polyglyceryl fatty acids, such as glyceryl mono-cotton seed oil fatty acid, glyceryl monoerucate, glyceryl sesquioleate, glyceryl monostearate, glyceryl α,α'-oleate pyroglutamate, and glyceryl monostearate malate; propylene glycol fatty acid esters such as monostearate propylene glycol; a hydrogenated castor oil derivative; a glycerin alkyl ether; and steareth-2.

Examples of the hydrophilic nonionic surfactant include POE-sorbitan fatty acid esters, such as POE-sorbitan monooleate, POE-sorbitan monostearate, POE-sorbitan monooleate and POE-sorbitan tetraoleate; POE sorbitol fatty acid esters, such as POE-sorbitol monolaurate, POE-sorbitol monooleate, POE-sorbitol pentaoleate and POE-sorbitol monostearate; POE-glycerin fatty acid esters, such as POE-glycerin monostearate, POE-glycerin monoisostearate and POE-glycerin triisostearate; POE-fatty acid esters, such as POE-monooleate, POE-distearate, POE-monodioleate and ethylene glycol distearate; POE-alkyl ethers, such as POE-lauryl ether, POE-oleyl ether, POE-stearyl ether, POE-behenyl ether, POE-2-octyldodecyl ether and POE-cholestanol ether; Pluronic type surfactants (e.g., Pluronic); POE-POP-alkyl ethers, such as POE-POP-cetyl ether, POE-POP-2-decyltetradecyl ether, POE-POP-monobutyl ether, POE-POP-hydrogenated lanolin and POE-POP-glycerin ether; and steareth-21.

Examples of the metal sequestering agent include 1-hydroxyethane-1,1-diphosphonic acid; tetrasodium 1-hydroxyethane-1,1-diphosphate salt; disodium edetate; trisodium edetate; tetrasodium edetate; sodium citrate; sodium polyphosphate; sodium metaphosphate; gluconic acid; phosphoric acid; citric acid; ascorbic acid; succinic acid; edetic acid; and trisodium ethylenediaminehydroxyethyl triacetate.

Examples of the polyhydric alcohol include a dihydric alcohol, such as ethylene glycol, propylene glycol, pentylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; a trihydric alcohol, such as glycerin and trimethylolpropane; a tetrahydric alcohol such as pentaerythritol (e.g., 1,2,6-hexanetriol); a pentahydric alcohol such as xylitol; a hexahydric alcohol, such as sorbitol and mannitol; a polyhydric alcohol polymer, such as diethylene glycol, dipropylene glycol, triethylene glycol, polypropylene glycol and tetraethylene glycol; dihydric alcohol alkyl ethers, such as ethylene glycol monomethyl ether and ethylene glycol monoethyl ether; dihydric alcohol alkyl ethers, such as diethylene glycol monomethyl ether, diethylene glycol monoethyl ether and diethylene glycol monobutyl ether; a dihydric alcohol ether ester, such as ethylene glycol monomethyl ether acetate and ethylene glycol monoethyl ether acetate; a glycerol monoalkyl ether, such as chimyl alcohol, selachyl alcohol and batyl alcohol; and a sugar alcohol, such as sorbitol, maltitol, maltotriose, mannitol, sucrose, erythritol, glucose, fructose, starch sugar, maltose, xylitose, and a reduced alcohol of a starch sugar.

Examples of the monosaccharide include a triose, such as D-glyceryl aldehyde and dihydroxyacetone; a tetrose, such as D-erythrose, D-erythrulose, D-threose and erythritol; a pentose, such as L-arabinose, D-xylose, L-lyxose, D-arabinose, D-ribose, D-ribulose, D-xylulose and L-xylulose; a hexose, such as D-glucose, D-talose, D-psicose, D-galactose, D-fructose, L-galactose, L-mannose and D-tagatose; a heptose, such as aldoheptose and heprose; an octose such as octurose; a deoxy sugar, such as 2-deoxy-D-ribose, 6-deoxy-L-galactose and 6-deoxy-L-mannose; an amino sugar, such as D-glucosamine, D-galactosamine, sialic acid, amino uronic acid and muramic acid; and a uronic acid, such as D-glucuronic acid, D-mannuronic acid, L-guluronic acid, D-galacturonic acid and L-iduronic acid.

Examples of the oligosaccharide include sucrose, lactose, maltose, trehalose, cellobiose, gentiobiose, umbilicin, raffinose, gentianose, maltotriose, melezitose, planteose, unbelliferose, stachyose, and verbascose.

Examples of the amino acid include a neutral amino acid, such as threonine and cysteine; and a basic amino acid such as hydroxylysine. Further, as an amino acid derivative, for example, sodium acyl sarcosinate (sodium lauroyl sarcosinate), acyl glutamate, sodium acyl β-alanine, glutathione, and pyrrolidone carboxylic acid may be exemplified.

Examples of the organic amine include monoethanolamine, diethanolamine, triethanolamine, morpholine, triisopropanolamine, 2-amino-2-methyl-1,3-propanediol, and 2-amino-2-methyl-1-propanol.

Examples of the polymer emulsion include an acrylic resin emulsion, a poly(ethyl acrylate) emulsion, an acrylic resin solution, a poly(alkyl acrylate) emulsion, a poly(vinyl acetate) resin emulsion, and a natural rubber latex.

Examples of the vitamins include vitamins A, $B_1$, $B_2$, $B_6$, C and E and derivatives thereof, pantothenic acid and derivatives thereof and biotin.

Examples of the antioxidants include ascorbic acid and derivatives thereof such as ascorbyl palmitate, ascorbyl tetraisopalmitate, ascorbyl glucoside, magnesium ascorbyl phosphate, sodium ascorbyl phosphate and ascorbyl sorbate; tocopherol and derivatives thereof, such as tocopheryl acetate, tocopheryl sorbate, and other esters of tocopherol; dibutyl hydroxytoluene (BHT) and butylated hydroxyanisole (BHA); gallic acid ester; phosphoric acid; citric acid; maleic acid; malonic acid; succinic acid; fumaric acid; cephalin; a hexametaphosphate; phytic acid; ethylenediaminetetraacetic acid; and plant extracts, for instance from *Chondrus cripsus, Rhodiola, Thermus thermophilus*, mate leaves, oak wood, kayu rapet bark, sakura leaves and ylang ylang leaves.

Examples of the moisturizing agent include polyethylene glycol; propylene glycol; dipropylene glycol; glycerin; 1,3-butylene glycol; xylitol; sorbitol; maltitol; mucopolysaccharides such as chondroitin sulfuric acid; hyaluronic acid; sodium hyaluronate; sodium acetyl hyaluronate; mucoitinsulfuric acid; caronic acid; atelo-collagen; cholesteryl-12-hydroxystearate; a bile salt; a main component of NMF (natural moisturizing factor), such as a pyrrolidone carboxylic acid salt and a lactic acid salt; amino acids such as urea, cysteine and serine; short-chain soluble collagen; a diglycerin (EO) PO addition product; homo- or copolymers of 2-methacryloyloxyethylphosphorylcholine commercially available from NOF Corporation under the name of, for example, Lipidure HM and Lipidure PBM; panthenol; allantoin; PEG/PPG/Polybutylene Glycol-8/5/3 Glycerin commercially available from NOF Corporation under the trade name of Wilbride S 753; trimethylglycine commercially available from Asahi Kasei Chemicals Corporation under the trade name of AMINOCOAT; and various plant extracts such as Castanea sativa extracts, hydrolyzed hazelnut proteins, *Polianthes tuberosa* polysaccharides, *Argania spinosa* kernel oil, and an extract of pearl containing conchiolin commercially available from Maruzen Pharmaceuticals Co., Ltd. under the trade name of Pearl Extract®.

Examples of the skin softener include glyceryl polymethacrylate and methyl gluceth-20.

Examples of the antiaging agent include acyl amino acids (specifically, products commercially available from SEDERMA, S.A.S. under the trade name of Maxilip, Matrixyl 3000 or Biopeptide CL, or product commercially available from SEPPIC under the trade name of Sepilift); *Pisum sativum* extracts; hydrolyzed soy proteins; methylsilanol mannuronate; hydrolyzed cucurbita pepo seedcake; and *Scenedesmus* extracts.

Examples of the anti-pollution agents include Moring a pterygosperma seed extracts (specifically, such as a product commercially available from LSN under the trade name of Purisoft); and Shea butter extracts (specifically, for example, products commercially available from SILAB under the trade name of Detoxyl, a blend of an ivy extract, phytic acid and a sunflower seed extract (for example, a product commercially available from SEDERMA, S.A.S. under the trade name of OSMOPUR)).

Examples of the keratolytic agents include α-hydroxy acids (specifically, for example, glycolic, lactic, citric, malic, mandelic and tartaric acids), β-hydroxy acids (specifically, for example, salicylic acid), esters thereof (specifically, $C_{12-13}$ alkyl lactate), and plant extracts containing these hydroxy acids (specifically, for example, *Hibiscus sabdriffa* extracts).

Examples of the water-soluble polymer include natural polymers such as Arabian gum, carrageenan, karaya gum, tragacanth gum, Quinn seed (marmelo), casein, dextrin, gelatine, sodium pectate, sodium alginate, locust bean gum, guar gum, tala gum, Tamarind gum, glucomannan, xylan, mannan, xanthan gum, agar, pectin, fucoidan, galactomannan, curdlan, gellan gum, fucogel, casein, collagen, starch, sodium hyaluronate and Alcasealan (*Alcaligenes polysaccharides*), semi-synthetic polymers such as methylcellulose, ethylcellulose, sodium carboxymethylcellulose, hydroxyethylcellulose, hydroxymethylcellulose, hydroxypropylcellulose, methylhydroxypropylcellulose, hydroxypropylmethylcellulose stearoyl ester, propylene glycol alginate and cellulose dialkyldimethylammonium sulfate, and synthetic polymers such as PVA (polyvinyl alcohol), PVM (polyvinyl methyl ether), PVP (polyvinylpyrrolidone), polyethylene oxide, sodium polyacrylate, carboxyvinyl polymer, acrylate/$C_{10-30}$ alkyl acrylate crosspolymer, and sodium polyacrylate.

Examples of clay minerals as the thickener include bentonite, hectorite, magunesium aluminum silicate (veegum) and laponite.

Examples of the anti-inflammatory agents include bisabolol, allantoin, tranexamic acid, zinc oxide, sulfur oxide and derivatives thereof, chondroitin sulfate, and glycyrrhizinic acid and derivatives thereof (for example, glycyrrhizinates).

The oil-in-water emulsion composition of the present invention may also contain at least one whitening agent to block the synthesis of structural proteins such as the melanocyte-specific protein Pmel17 involved in the mechanism of melanogenesis (stage I). Examples of such a whitening agent include the ferulic acid-containing cytovector (water, glycol, lecithin, ferulic acid, hydroxyethylcellulose) commercially available from BASF under the trade name of Cytovector®.

Furthermore, the oil-in-water emulsion composition of the present invention may contain at least one peptide as described in WO2009/010356.

Furthermore, the oil-in-water emulsion composition of the present invention may include a whitening agent having an inhibitory effect on melanin synthesis, on nanophthalmia-related transcription factor expression, on an anti-tyrosinase activity and/or on endothelin-1 synthesis. Examples of such a whitening agent include a *Glycyrrhiza glabra* extract commercially available from Maruzen Pharmaceuticals Co., Ltd. under the trade name of Licorice Extract®.

Furthermore, the oil-in-water emulsion composition of the present invention may include whitening agents having an antioxidant action as well, such as vitamin C compounds, which include ascorbate salts, ascorbyl esters of fatty acids or of sorbic acid, and other ascorbic acid derivatives. Specific examples include ascorbyl phosphates (magnesium ascorbyl phosphate, sodium ascorbyl phosphate, and the like), and saccharide esters of ascorbic acid (ascorbyl-2-glucoside, 2-O-α-D-glucopyranosyl L-ascorbate, 6-O-β-D-galactopyranosyl L-ascorbate, and the like). Active agents of this type are commercially available from DKSH under the trade name of Ascorbyl Glucoside®.

Furthermore, the oil-in-water emulsion composition of the present invention may include other whitening agents. Examples of the other whitening agents include pigmentation inhibiting agents such as plant extracts (e.g., Narcissus tazetta extracts), cetyl tranexamate (Nikko Chemicals Co., Ltd; trade name: NIKKOL TXC), arbutin, kojic acid, ellagic acid, cysteine, 4-thioresorcin, resorcinol or rucinol or derivatives thereof, glycyrrhizinic acid and hydroquinone-β-glucoside.

Furthermore, the oil-in-water emulsion composition of the present invention may also include organic and/or inorganic sunscreens.

Examples of the organic sunscreens include dibenzoylmethane derivatives such as butyl methoxydibenzoylmethane (for example, a product commercially available from HOFFMANN LA ROCHE under the trade name of Parsol 1789); cinnamic acid derivatives such as octyl methoxycinnamate (for example, a product commercially available from HOFFMANN LA ROCHE under the trade name of Parsol MCX), salicylates, para-aminobenzoic acids; β,β'-diphenylacrylate derivatives; benzophenone derivatives; benzylidenecamphor derivatives such as terephtalylidene dicamphor sulphonic acid; phenylbenzimidazole derivatives; triazine derivatives; phenylbenzotriazole derivatives; and anthranilic acid derivatives, all of which may be coated or encapsulated.

Examples of the inorganic sunscreens include pigments and nanopigments formed from coated or uncoated metal oxides. Examples of the nanopigments include titanium oxide, iron oxide, zinc oxide, zirconium oxide and cerium oxide nanopigments, which are all well-known as UV photoprotective agents.

Examples of the antiseptic agent include p-hydroxybenzoate ester (e.g., methylparaben and propylparaben) and phenoxyethanol.

In addition, as optional ingredient to be used in the oil-in-water emulsion composition of the present invention, those mentioned in the International Cosmetic Ingredient Dictionary and Handbook, 13th Edition, 2010, published by the Personal Care Products Council, can be used.

The amounts of these optional ingredients contained are not particularly limited as long as the optional ingredients are in a range which does not impair the object of the present invention, but particularly the amount of the oil-soluble material contained is desirably used in a range which does not inhibit the stable dispersion of emulsification particles. The amounts of the optional ingredients contained are appropriately selected depending on the formulation or product form.

The oil-in-water emulsion composition of the present invention can be produced by first preparing an oil phase comprising:
A) a physiologically acceptable salt of a tranexamate ester,
B) an amphiphilic substance,
C) an oily substance and
D) water, a water-soluble organic solvent or a mixture thereof
wherein the weight ratio of the ingredients A:B is in the range of 1:0.5 to 1:2.5 and the weight ratio of the ingredients A:C in is the range of 1:1 to 1:5.0, and the weight ratio of the ingredients A:D is 1:0.2 to 1:5.0; and
then adding the obtained oil phase to a water phase comprising
E) water, a water-soluble organic solvent or a mixture thereof.

First, an oil phase is prepared. In the present invention, an oil-in-water type emulsion composition can be obtained by an ordinary mixing operation by using the ingredients A, B and C at a specific quantitative ratio. As mentioned above, the quantitative ratio of the ingredients A and B is ingredient A:ingredient B=1:0.5 to 1:2.5, preferably 1:1.0 to 1:2.0, more preferably 1:1.5 to 1:2.0 by the weight ratio. The quantitative ratio of the ingredients A and C is ingredient A:ingredient C=1:1 to 1:5.0, preferably 1:2.0 to 1:4.0, more preferably 1:2.5 to 1:3.5 by the weight ratio. Oil-soluble optional ingredients may be added to the oil phase beforehand with the proviso that the optional ingredients do not inhibit the stability of the emulsification particles.

A small amount of the aqueous medium (that is, water, a water-soluble organic solvent or a mixture thereof) is added to the oil phase beforehand in the present invention. The addition of a small amount of the aqueous medium presumably enables alignment of the oil-soluble moieties (lipophilic parts of the oily substance, the tranexamate salt and the amphiphilic substance) and the water-soluble moieties (hydrophilic parts of the aqueous medium, the tranexamate salt and the amphiphilic substance) to some extent, which promotes formation of uniform emulsification particles when the oil phase is added to the water phase. The amount of the aqueous medium is an amount in which the weight ratio of ingredient A (tranexamate ester salt): ingredient D (water, a water-soluble organic solvent or a mixture thereof) is in the range of 1:0.2 to 1:5.0, preferably 1:0.5 to 1:4.0 and more preferably 1:1.0 to 1:3.0.

Then the obtained oil phase is added to the water phase containing water, a water-soluble organic solvent or a mixture thereof.

The amount of water, the water-soluble organic solvent or the mixture thereof for use in the water phase is not particularly limited but the total of the content of water, the water-soluble organic solvent or the mixture thereof and the water-soluble ingredient is adjusted to a range of preferably 40 to 95% by weight, more preferably 50 to 90% by weight, and particularly preferably 60 to 80% by weight based on the total weight of the oil-in-water type emulsion composition of the present invention. The amount of the solvent used can be appropriately determined according to the usage of the oil-in-water type emulsion composition and the like. The water-soluble optional ingredients may be added to the water phase beforehand.

The weight ratio of the oil phase:the water phase is not particularly limited, but a range of 1:1 to 1:30 is preferable, a range of 1:1 to 1:10 is more preferable and a range of 1:2 to 1:4 is particularly preferable.

It is preferable to heat and dissolve the oil phase and the water phase before adding the oil phase to the water phase. The heating temperature is preferably in the range of 75 to 95° C., more preferably in the range of 77 to 93° C., and particularly preferably in the range of 80 to 90° C. More uniform emulsification particles can be obtained by having heated and dissolved the oil phase and the water phase.

After the oil phase and the water phase are mixed, an emulsion composition can be obtained by cooling the mixture to room temperature under stirring. Optional ingredients may be further incorporated in the obtained emulsion composition to such an extent that the optional ingredients do not impair the object of the present invention.

The oil-in-water emulsion composition of the present invention can be produced as above. According to the present invention, an oil-in-water emulsion composition in which fine emulsification particles are dispersed can be obtained by an ordinary mixing operation without using a special device. According to a preferable aspect of the present invention, the appearance of the oil-in-water type emulsion composition of the present invention is semitransparent. This means that fine emulsification particles are dispersed in a uniform state in the aqueous medium.

According to a preferable aspect of the present invention, the average particle size of the emulsified particles in the oil-in-water type emulsion composition of the present invention is 12 nm to 100 nm, preferably 12 nm to 80 nm, and more preferably 12 nm to 60 nm.

The oil-in-water emulsion composition of the present invention can be preferably used as a composition for external use such as drugs, quasi drugs and cosmetic products. The product form of the composition for external use is arbitrarily selectable. For example, the composition is applicable to facial cosmetic materials, such as a facial cleanser, a face lotion, an essence liquid, a milky lotion, a cream and a pack; makeup cosmetic materials, such as a foundation, a lipstick and an eye shadow; body cosmetic materials; hair care cosmetic materials; oral care toiletries; perfumeries; body cleansers; and ointments.

The preferable weight ratio of the tranexamate ester salt: the amphiphilic substance:the oily substance does not change depending on the product form. The preferable amount of the oil phase (in particular, weight of the ingredients A, B and C) in the whole oil-in-water type emulsion composition of the present invention is preferably adjusted according to the product form.

For example, when the oil-in-water emulsion composition of the present invention is used as a skin lotion, the weight of the oil phase including the tranexamate ester salt, the amphiphilic substance and the oily substance based on the total weight of the oil-in-water type emulsion composition of the present invention is preferably 1 to 20% by weight and more preferably 5 to 15% by weight.

In addition, for example, when the oil-in-water type emulsion composition of the present invention is used as a serum, the weight of the oil phase including the tranexamate ester salt, the amphiphilic substance and the oily substance based on the total weight of the oil-in-water type emulsion composition of the present invention is preferably 5 to 30% by weight and more preferably 10 to 25% by weight.

In addition, for example, when the oil-in-water type emulsion composition of the present invention is used as a gel-like milky lotion, the weight of the oil phase including the tranexamate ester salt, the amphiphilic substance and the oily substance based on the total weight of the oil-in-water type emulsion composition of the present invention is preferably 10 to 30% by weight and more preferably 10 to 25% by weight.

In addition, for example, when the oil-in-water type emulsion composition of the present invention is used as a cream, the weight of the oil phase including the tranexamate ester salt, the amphiphilic substance and the oily substance based on the total weight of the oil-in-water type emulsion composition of the present invention is preferably 10 to 40% by weight and more preferably 20 to 35% by weight.

The above values are shown as a guide, and the preferable amount of the oil phase in the whole oil-in-water type emulsion composition can be appropriately adjusted according to the intended use of the composition.

Since the oil-in-water type emulsion composition of the present invention contains a tranexamate ester salt having a whitening effect, topical application thereof to the skin can exhibit the effect of inhibiting pigmentation of and/or whitening the skin. That is, the present invention provides a cosmetic method which inhibits pigmentation of and/or whitens the skin by topical application, to the skin, of the composition for external use of the present invention.

According to a preferable aspect of the present invention, an effect indicating that inhibition of pigmentation and/or whitening of the skin can be performed to reduce aging spots or pigmentation can be achieved by using the oil-in-water type emulsion composition of the present invention as a cosmetic material.

EXAMPLES

In the following, the present invention will be described by way of Examples and Comparative Examples but the present invention is not limited to these Examples.

Examples 1, 2 and Comparative Examples 1 to 4

Compositions for external use shown in Table 1 were prepared as follows. Here, stirring was performed with a stirring rod by hand.

1) Ingredients 1 to 6 were heated, stirred and dissolved at 85±5° C. (mixture 1 which is an oil phase component).
2) Next, ingredient 7 was maintained at 85±5° C. and the mixture 1 mentioned above was added thereto under stirring.
3) After that, the obtained mixture was cooled to room temperature (25±5° C.) under stirring.

TABLE 1

| | Unit: % by weight | | | | | |
|---|---|---|---|---|---|---|
| Ingredient | Example 1 | Example 2 | Comparative Example 1 | Comparative Example 2 | Comparative Example 3 | Comparative Example 4 |
| 1. Cetyl tranexamate hydrochloride[*1] | 1.0 | 1.0 | — | — | — | 1.0 |
| 2. Glyceryl monostearate | 1.5 | — | — | 1.5 | 1.5 | — |
| 3. Cetyl alcohol | — | 1.0 | 1.0 | — | 1.0 | — |
| 4. Squalane | 3.0 | 3.0 | 3.0 | 3.0 | 3.0 | 3.0 |
| 5. Dipropylene glycol | 1.0 | 1.0 | 1.0 | 1.0 | 1.0 | 1.0 |
| 6. Purified water | 1.0 | 1.0 | 1.0 | 1.0 | 1.0 | 1.0 |
| 7. Purified water | Balance | Balance | Balance | Balance | Balance | Balance |
| Total | 100 | 100 | 100 | 100 | 100 | 100 |

[*1]"NIKKOL TXC" (trade name, produced by Nikko Chemicals Co., Ltd.) was used.
Appearance: White to slightly yellowish crystalline powder
Melting point: 131 to 135° C., weight loss on drying: 1.0% or less (at 105° C., for 2 hours)

[Appearance and Particle Size after Preparation]

The respective compositions for external use after the preparation were left at room temperature (20 to 25° C.) overnight and the presence/absence of separation and transparency were checked by visual observation. In addition, the particle size distribution was measured with a laser diffraction particle size distribution measuring apparatus (SALD-7000 manufactured by SHIMADZU Corporation) in order to know the particle size.

When a sample is placed into a flow cell filled with distilled water beforehand where the water is circulated, optical intensity distribution changes depending on the amount placed. The sample was placed up to an appropriate concentration in which the maximum value of the optical intensity distribution became 35 to 75%, and the particle size distribution was measured. The appearance checked by visual observation and the measured values of the particle size distribution are shown in Table 2.

TABLE 2

|  | Example 1 | Example 2 | Comparative Example 1 | Comparative Example 2 | Comparative Example 3 | Comparative Example 4 |
|---|---|---|---|---|---|---|
| Appearance after left at room temperature overnight after preparation | Semi-transparent | Semi-transparent | Separated | Separated | Clouded | Separated |
| Particle size distribution (median particle size, μm) | 0.043 | 0.031 | —* | —* | 46.20 | —* |

*The obtained composition for external use was separated and nonuniform, and thus measurement of the particle size distribution with the laser diffraction particle size distribution measuring apparatus was not possible.

As shown in Table 2, as for the compositions for external use of Examples 1 and 2, compositions for external use with semitransparent appearance were obtained after having incorporated oily substances insoluble in water. In addition, the measured values of the particle size distribution of the compositions for external use of Examples 1 and 2 were less than 0.100 μm (100 nm) as the median particle size.

Example 3 and Comparative Example 5

Compositions for external use shown in Table 3 were prepared as follows. Here, stirring was performed with a stirring rod by hand.
1) Oil phase ingredients 1 to 10 were heated, stirred and dissolved at 85±5° C. (mixture 1 which is an oil phase ingredient).
2) Water phase ingredients 11 to 13 were heated, stirred and dissolved at 85±5° C. (mixture 2 which is a water phase ingredient).
3) Mixture 1 was added to mixture 2 maintained at 85±5° C. under stirring.
4) After that, the obtained mixture was cooled to room temperature (25±5° C.) under stirring.

[Appearance and Particle Size after Preparation]

The respective compositions for external use after preparation were left at room temperature (20 to 25° C.) overnight and the presence/absence of separation and transparency were checked by visual observation. In addition, the particle size distribution was measured with a laser diffraction particle size distribution measuring apparatus (SALD-7000 manufactured by SHIMADZU Corporation) by the same method as above. The appearance checked by visual observation, appearance photographs taken with a digital camera and the measured values of particle size distribution are shown in FIG. 1.

As shown in FIG. 1, the composition for external use of Comparative Example 5, which does not contain cetyl tranexamate hydrochloride, showed a white appearance as seen in an ordinary milky lotion. On the other hand, the composition for external use of Example 3 showed a semitransparent appearance. In addition, the measured value of the particle size distribution of the composition for external use of Comparative Example 5 in the form of a milky lotion was 37 μm as the median particle size, whereas the measured value of the particle size distribution of the composition for external use of Example 3 was 0.043 μm, which is less than 100 nm, as the median particle size.

Although the composition for external use of the present invention contains oily ingredients, the composition showed a semitransparent appearance, and therefore the composition could be used as a skin lotion or a serum having a high moisture retention and the invention widened the formulation form.

TABLE 3

| | | Unit: % by weight | |
|---|---|---|---|
| | Ingredients | Comparative Example 5 | Example 3 |
| Oil phase ingredients | 1. Cetyl tranexamate hydrochloride*[1] | — | 3.0 |
| | 2. Polyethylene glycol monostearate | 1.5 | 1.5 |
| | 3. Cetyl alcohol | 2.5 | 2.5 |
| | 4. Glycerin monostearin ether | 0.5 | 0.5 |
| | 5. Glyceryl monostearate | 1.5 | 1.5 |
| | 6. Cetyl isooctanoate | 7.0 | 7.0 |
| | 7. Squalane | 3.0 | 3.0 |
| | 8. BHT | 0.05 | 0.05 |
| | 9. Dipropylene glycol | 3.0 | 3.0 |
| | 10. Purified water | 3.0 | 3.0 |
| Water phase ingredients | 11. 1,3-Butylene glycol | 3.0 | 3.0 |
| | 12. Methylparaben | 0.2 | 0.2 |
| | 13. Purified water | Balance | Balance |
| | Total | 100 | 100 |

*[1]"NIKKOL TXC" (trade name, produced by Nikko Chemicals Co., Ltd.) was used.
Appearance: White to slightly yellow crystalline powder
Melting point: 131 to 135° C., weight loss on drying: 1.0% or less (at 105° C. for 2 hours)

Examples 4

Method for Preparing Skin Lotions 1 to 4

Compositions for external use which were skin lotions 1 to 4 containing oily substances shown in Table 5 were prepared as follows. Here, stirring was performed with a stirring rod by hand.

1) Oil phase ingredients 1 to 9 were heated, stirred and dissolved at 85±5° C. (mixture 1 which is an oil phase ingredient).
2) Water phase ingredients 10 to 15 were heated, stirred and dissolved at 85±5° C. (mixture 2 which is a water phase ingredient).
3) Mixture 1 was added to mixture 2 maintained at 85±5° C. under stirring (mixture 3).
4) Cooling was started while stirring mixture 3 and, ingredients 16 to 19, which were active ingredients, and ingredient 20 (fragrance) were sequentially added at 30±5° C.

TABLE 5

|  | Ingredients | Skin lotion 1 | Skin lotion 2 | Skin lotion 3 | Skin lotion 4 |
|---|---|---|---|---|---|
| Oil phase ingredients | 1. Cetyl tranexamate hydrochloride*[1] | 1.0 | 1.0 | 2.0 | 3.0 |
|  | 2. Polyethylene glycol monostearate | 0.5 | 0.2 | — | 1.0 |
|  | 3. Cetyl alcohol | 1.0 | — | — | — |
|  | 4. Behenyl alcohol | — | 1.0 | 2.0 | 3.0 |
|  | 5. Squalane | 2.5 | 1.0 | 2.0 | 2.0 |
|  | 6. Dimethylpolysiloxane (6cs) | — | 0.5 | 1.0 | 1.5 |
|  | 7. Cetyl isooctanoate | — | 1.0 | 2.0 | 4.0 |
|  | 8. Dipropylene glycol | 1.0 | 1.0 | 2.0 | 3.0 |
|  | 9. Purified water | 1.0 | 1.0 | 2.0 | 3.0 |
| Water phase ingredients | 10. Ethanol | — | 5.0 | — | — |
|  | 11. 1,3-Butylene glycol | 2.0 | — | 2.0 | 2.0 |
|  | 12. Glycerin | — | — | 2.0 | 5.0 |
|  | 13. Raffinose | 1.0 | 1.0 | 1.0 | — |
|  | 14. Methylparaben | 0.2 | 0.2 | 0.2 | 0.2 |
|  | 15. Purified water | Balance | Balance | Balance | Balance |
| Active ingredients | 16. Licorice extract | — | 1.0 | — | 1.0 |
|  | 17. Narcissus tazetta bulb extract | — | 1.0 | — | 1.0 |
|  | 18. Peptide | — | 1.0 | — | 1.0 |
|  | 19. Pearl extract | — | 1.0 | — | 1.0 |
|  | 20. Fragrance | — | 0.10 | 0.10 | — |
|  | Total | 100 | 100 | 100 | 100 |

Unit: % by weight

*[1] "NIKKOL TXC" (trade name, produced by Nikko Chemicals Co., Ltd.) was used.
Appearance: White to slightly yellow crystalline powder
Melting point: 131 to 135° C., weight loss on drying: 1.0% or less (at 105° C. for 2 hours)

[Appearance and Particle Size after Preparation]

The respective skin lotion compositions after preparation were left at room temperature (20 to 25° C.) overnight and the presence/absence of separation and transparency were checked by visual observation. In addition, the particle size distribution was measured with a laser diffraction particle size distribution measuring apparatus (SALD-7000 manufactured by SHIMADZU Corporation) by the same method as above. The appearance checked by visual observation and the measured valued of particle size distribution are shown in Table 6.

TABLE 6

|  | Skin lotion 1 | Skin lotion 2 | Skin lotion 3 | Skin lotion 4 |
|---|---|---|---|---|
| Appearance after left at room temperature overnight after preparation | Semitransparent | Semitransparent | Semitransparent | Semitransparent |
| Particle size distribution (median particle size, μm) | 0.031 | 0.031 | 0.032 | 0.031 |

As shown in Table 6, as for the compositions for external use which were skin lotions 1 to 4, compositions for external use having a semitransparent appearance were obtained after having incorporated oily substances insoluble in water. In addition, the measured values of the particle size distribution of this composition for external use were each less than 0.100 μm (100 nm) as the median particle size.

Examples 5

Method for Preparing Sera 2 to 6

Serum compositions for external use shown in Table 7 were prepared as follows. Here, stirring was performed with a stirring rod by hand.

1) Oil phase ingredients 1 to 12 were heated, stirred and dissolved at 85±5° C. (mixture 1 which is an oil phase ingredient).

2) Water phase ingredients 13 to 15 were heated, stirred and dissolved at 85±5° C. (mixture 2 which is a water phase ingredient).

3) Mixture 1 was added to mixture 2 maintained at 85±5° C. under stirring (mixture 3).

4) Cooling was started while stirring the mixture 3 and, ingredients 16 to 19, which were active ingredients, and ingredient 20 (fragrance) were sequentially added at 30±5° C.

TABLE 7

| | | Unit: % by weight | | | | |
|---|---|---|---|---|---|---|
| Ingredients | | Serum 2 | Serum 3 | Serum 4 | Serum 5 | Serum 6 |
| Oil phase Ingredients | 1. Cetyl tranexamate hydrochloride[*1] | 2.0 | 2.0 | 3.0 | 3.0 | 3.0 |
| | 2. Polyethylene glycol monostearate | 1.0 | 1.0 | 1.0 | 1.0 | 1.0 |
| | 3. Cetyl alcohol | 2.0 | — | 2.5 | — | 3.0 |
| | 4. Stearyl alcohol | — | 2.0 | — | 2.5 | — |
| | 5. Glycerin monostearin ether | 1.0 | 1.0 | 1.5 | 1.5 | 1.0 |
| | 6. Cetyl isooctanoate | 4.5 | 3.5 | 7.0 | 4.5 | 5.5 |
| | 7. Squalane | 2.0 | 2.0 | 3.0 | 3.0 | 3.0 |
| | 8. Vaselin | — | 1.0 | — | 2.0 | — |
| | 9. Olive oil | — | — | — | — | 1.5 |
| | 10. BHT | 0.05 | 0.05 | 0.05 | 0.05 | 0.05 |
| | 11. Dipropylene glycol | 2.0 | 2.0 | 3.0 | 3.0 | 3.0 |
| | 12. Purified water | 2.0 | 2.0 | 3.0 | 3.0 | 3.0 |
| Water phase ingredients | 13. 1,3-Butylene glycol | 2.0 | 2.0 | 2.0 | 2.0 | 2.0 |
| | 14. Methylparaben | 0.2 | 0.2 | 0.2 | 0.2 | 0.2 |
| | 15. Purified water | Balance | Balance | Balance | Balance | Balance |
| Active ingredients | 16. Licorice extract | 0.1 | 0.1 | 0.1 | 0.1 | 0.1 |
| | 17. Narcissus tazetta bulb extract | 0.1 | 0.1 | 0.1 | 0.1 | 0.1 |
| | 18. Peptide | 0.1 | 0.1 | 0.1 | 0.1 | 0.1 |
| | 19. Pearl extract | 0.1 | 0.1 | 0.1 | 0.1 | 0.1 |
| 20. Fragrance | | 0.1 | 0.1 | 0.1 | 0.1 | 0.1 |
| Total | | 100 | 100 | 100 | 100 | 100 |

[*1]"NIKKOL TXC" (trade name, produced by Nikko Chemicals Co., Ltd.) was used.
Appearance: White to slightly yellow crystalline powder
Melting point: 131 to 135°C., weight loss on drying: 1.0% or less (at 105°C. for 2 hours)

[Appearance and Particle Size after Preparation]

The respective serum compositions after preparation were left at room temperature (20 to 25° C.) overnight and the presence/absence of separation and transparency were checked by visual observation. In addition, the particle size distribution was measured with a laser diffraction particle size distribution measuring apparatus (SALD-7000 manufactured by SHIMADZU Corporation) by the same method as above. The appearance checked by visual observation and the measured values of particle size distribution are shown in Table 8.

TABLE 8

| | Serum 2 | Serum 3 | Serum 4 | Serum 5 | Serum 6 |
|---|---|---|---|---|---|
| Appearance after left at room temperature overnight after preparation | Semitransparent | Semitransparent | Semitransparent | Semitransparent | Semitransparent |
| Particle size distribution (median particle size, μm) | 0.031 | 0.031 | 0.032 | 0.032 | 0.031 |

As shown in Table 8, as for the compositions for external use which were sera 2 to 6, compositions for external use having a semitransparent appearance were obtained after having incorporated oily substances insoluble in water. In addition, the measured values of the particle size distribution of these compositions for external use were each less than 0.100 μm (100 nm) as the median particle size.

Examples 6

Method for Preparing Semitransparent Milky Lotions 1 to 5

Compositions for external use which had an appearance of a semitransparent gel-like milky lotion and shown in Table 9 were prepared as follows. Here, stirring was performed with a stirring rod by hand.

1) Oil phase ingredients 1 to 10 were heated, stirred and dissolved at 85±5° C. (mixture 1 which is an oil phase ingredient).

2) Water phase ingredients 11 to 15 were heated, stirred and dissolved at 85±5° C. (mixture 2 which is a water phase ingredient).

3) Mixture 1 was added to mixture 2 maintained at 85±5° C. under stirring (mixture 3).
4) Cooling was started while stirring the mixture 3 and, any of ingredients 16 to 19, which were water-soluble polymers, was added thereto under stirring.

5) Furthermore, ingredients 20 to 23, which were active ingredients, ingredient 24 (phenoxyethanol), ingredient 25 (silicone powder) and ingredient 26 (fragrance) were sequentially added at 30±5° C.

TABLE 9

| | | Unit: % by weight | | | | |
|---|---|---|---|---|---|---|
| Ingredients | | Milky lotion 1 | Milky lotion 2 | Milky lotion 3 | Milky lotion 4 | Milky lotion 5 |
| Oil phase Ingredients | 1. Cetyl tranexamate hydrochloride[*1] | 2.0 | 2.0 | 2.0 | 3.0 | 3.0 |
| | 2. Polyethylene glycol monostearate | — | — | 1.0 | — | 1.0 |
| | 3. Cetyl alcohol | 2.0 | 2.0 | — | — | — |
| | 4. Cetostearyl alcohol | — | — | 2.0 | 2.0 | 3.0 |
| | 5. Squalane | 2.0 | 2.0 | 3.0 | 3.0 | 2.0 |
| | 6. Cetyl isooctanoate | 1.0 | 1.0 | 2.0 | 4.0 | — |
| | 7. 2-Oclyldodecyl myrislate | — | 1.5 | — | — | 4.0 |
| | 8. Dimethylpolysiloxane (6cs) | 1.5 | 1.5 | 1.5 | 2.0 | 2.0 |
| | 9. Dipropylene glycol | 2.0 | 2.0 | 2.0 | 3.0 | 3.0 |
| | 10. Purified water | 2.0 | 2.0 | 2.0 | 3.0 | 3.0 |
| Water phase ingredients | 11. 1,3-Butylene glycol | 2.0 | 2.0 | 2.0 | 2.0 | 2.0 |
| | 12. Glycerin | 2.0 | 2.0 | 2.0 | 2.0 | 2.0 |
| | 13. Raffinose | 1.0 | — | — | 1.0 | — |
| | 14. Methylparaben | 0.2 | 0.2 | — | — | 0.2 |
| | 15. Purified water | Balance | Balance | Balance | Balance | Balance |
| Water-soluble polymer | 16. Hydroxy methyl cellulose stearoyl ester (1% by weight aqueous solution) | — | 15.0 | — | — | — |
| | 17. Guar gum (1% by weight aqueous solution) | — | — | 20.0 | — | — |
| | 18. Tamarind gum (1% by weight aqueous solution) | — | — | — | 20.0 | — |
| | 19. PEG#4000 (20% by weight aqueous solution) | — | — | — | — | 10.0 |
| Active ingredients | 20. Licorice extract | — | — | 1.0 | 1.0 | 1.0 |
| | 21. Narcissus tazetta bulb extract | — | — | 1.0 | 1.0 | 1.0 |
| | 22. Peptide | — | — | 1.0 | 1.0 | 1.0 |
| | 23. Pearl extract | — | — | 0.1 | 0.1 | 1.0 |
| 24. Phenoxyethanol | | — | — | 0.20 | 0.20 | — |
| 25. Silicone powder[*2] | | — | — | — | — | 2.0 |
| 26. Fragrance | | — | — | 0.10 | 0.2 | — |
| Total | | 100 | 100 | 100 | 100 | 100 |

[*1]"NIKKOL TXC" (trade name, produced by Nikko Chemicals Co., Ltd.) was used.
Appearance: White to slightly yellow crystalline powder
Melting point: 131 to 135° C., weight loss on drying: 1.0% or less (at 105° C. for 2 hours)
[*2]"Tospearl 2000B" (trade name, produced by Momentive Performance Materials Inc.) was used.

Appearance: Truth spherical (average particle size: 6.0 μm), white fine particles

[Appearance and Particle Size After Preparation]

The respective milky lotion compositions after preparation were left at room temperature (20 to 25° C.) overnight and the presence/absence of separation and transparency were checked by visual observation. In addition, the particle size distribution was measured with a laser diffraction particle size distribution measuring apparatus (SALD-7000 manufactured by SHIMADZU Corporation) by the same method as above. The appearance checked by visual observation and the measured values of particle size distribution are shown in Table 10.

TABLE 10

| | Milky lotion 1 | Milky lotion 2 | Milky lotion 3 | Milky lotion 4 | Milky lotion 5 |
|---|---|---|---|---|---|
| Appearance after left at room temperature overnight after preparation | Semitransparent | Semitransparent | Semitransparent | Semitransparent | Semitransparent |

TABLE 10-continued

|  | Milky lotion 1 | Milky lotion 2 | Milky lotion 3 | Milky lotion 4 | Milky lotion 5 |
|---|---|---|---|---|---|
| Particle size distribution (median particle size, μm) | 0.031 | 0.039 | 0.032 | 0.032 | 0.040 |

As shown in Table 10, as for the compositions for external use which were milky lotions 1 to 5, compositions for external use having a semitransparent appearance were obtained after having incorporated oily substances insoluble in water. In addition, the measured values of the particle size distribution of these compositions for external use were each less than 0.100 μm (100 nm) as the median particle size.

Example 7

Method for Preparing Semitransparent Creams 1 to 4

Compositions for external use which had an appearance of semitransparent gel-like cream shown in Table 11 were prepared as follows. Here, stirring was performed with a propeller-type stirring rod (Three One Motor, 600 to 800 rpm) since the mixtures had high viscosity.
1) Oil phase ingredients 1 to 11 were heated, stirred and dissolved at 85±5° C. (mixture 1 which is an oil phase ingredient).
2) Water phase ingredients 12 to 15 were heated, stirred and dissolved at 85±5° C. (mixture 2 which is a water phase ingredient).
3) Mixture 1 was added to mixture 2 maintained at 85±5° C. under stirring (mixture 3).
4) Cooling was started while stirring the mixture 3 and ingredient 16 (fragrance) was sequentially added at 30±5° C.

TABLE 11

|  |  | Unit: % by weight | | | |
|---|---|---|---|---|---|
|  | Ingredients | Cream 1 | Cream 2 | Cream 3 | Cream 4 |
| Oil phase ingredients | 1. Cetyl tranexamate hydrochloride*[1] | 3.0 | 3.0 | 3.0 | 5.0 |
|  | 2. Polyoxyethylene (20) sorbitan monooleate | — | 1.5 | 1.5 | 2.0 |
|  | 3. Cetyl alcohol | 3.0 | 3.0 | 2.5 | 4.0 |
|  | 4. Glyceryl monostearate | — | — | 1.0 | 2.0 |
|  | 5. Glycerin monostearyl ether | — | — | 1.0 | — |
|  | 6. Glycerin monocetyl ether | — | 1.4 | — | — |
|  | 7. Squalane | 7.5 | 3.0 | 3.0 | 15.0 |
|  | 8. 2-Octyldodecyl myristate | — | 7.0 | 7.0 | — |
|  | 9. BHT | 0.05 | 0.05 | 0.05 | 0.05 |
|  | 10. Dipropylene glycol | 3.0 | 3.0 | 3.0 | 5.0 |
|  | 11. Purified water | 3.0 | 3.0 | 3.0 | 5.0 |
| Water phase ingredients | 12. 1,3-Butylene glycol | — | — | 2.0 | 2.0 |
|  | 13. Glycerin | — | — | — | 2.0 |
|  | 14. Methylparaben | — | — | 0.2 | 0.2 |
|  | 15. Purified water | Balance | Balance | Balance | Balance |
|  | 16. Fragrance | — | — | 0.20 | 0.20 |
|  | Total | 100 | 100 | 100 | 100 |

*[1]"NIKKOL TXC" (trade name, produced by Nikko Chemicals Co., Ltd.) was used.
Appearance: White to slightly yellow crystalline powder
Melting point: 131 to 135° C., weight loss on drying: 1.0% or less (at 105° C. for 2 hours)

[Appearance and Particle Size after Preparation]

The respective cream compositions after preparation were left at room temperature (20 to 25° C.) overnight and the presence/absence of separation and transparency were checked by visual observation. In addition, the particle size distribution was measured with a laser diffraction particle size distribution measuring apparatus (SALD-7000 manufactured by SHIMADZU Corporation) by the same method as above. The appearance checked by visual observation and the measured values of particle size distribution are shown in Table 12.

TABLE 12

|  | Cream 1 | Cream 2 | Cream 3 | Cream 4 |
|---|---|---|---|---|
| Appearance after left at room temperature overnight after preparation | Semitransparent | Semitransparent | Semitransparent | Semitransparent |
| Particle size distribution (median particle size, μm) | 0.031 | 0.032 | 0.032 | 0.031 |

As shown in Table 12, as for the compositions for external use which were creams 1 to 4, compositions for external use having a semitransparent appearance were obtained after having incorporated a large amount of oily substances insoluble in water. In addition, the measured values of the particle size distribution of these compositions for external use were each less than 0.100 μm (100 nm) as the median particle size.

INDUSTRIAL APPLICABILITY

The oil-in-water type emulsion composition of the present invention is favorably applicable to drugs, quasi drugs and cosmetic products. A fresh and refreshing feeling of use can be obtained when applied to the skin or hair as well as a smooth and soft feeling of use imparting wet moisture to the skin or hair can be obtained after applied, by using an oil-in-water type emulsion composition of the present invention. The oil-in-water type emulsion composition of the present invention can be used in various product forms. According to a preferable aspect of the present invention, the composition for external use of the present invention can exhibit the effects of inhibiting pigmentation of and/or whitening the skin by topical application thereof to the skin.

The invention claimed is:

1. An oil-in-water emulsion composition comprising emulsified particles in an aqueous medium, said emulsified particles comprising:
an oil phase comprising
A) a physiologically acceptable salt of a tranexamate ester,
B) an amphiphilic substance,
C) an oily substance, and
D) water, a water-soluble organic solvent or a mixture thereof, wherein a weight ratio of the ingredients A:B is in the range of 1:1 to 1:2, a weight ratio of the ingredients A:C is in the range of 1:1 to 1:5.0, and a weight ratio of the ingredients A:D is 1:0.2 to 1:5.0; and wherein the emulsified particles have an average particle size, based on median diameter, of 12 nm to 100 nm.

2. The composition according to claim 1, wherein the tranexamate ester is represented by the following formula (1):

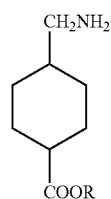

(1)

wherein R represents a linear or branched, saturated or unsaturated hydrocarbon group having 1 to 22 carbon atoms, which may be substituted by a substituent selected from a hydroxyl group and an amino group.

3. The composition according to claim 2, wherein the physiologically acceptable salt of a tranexamate ester is cetyl tranexamate hydrochloride.

4. The composition according to claim 2, wherein the amphiphilic substance comprises at least one substance selected from a group consisting of alcohols, fatty acids, fatty acid esters, fatty acid ethers, glycerin fatty acid esters and glycerin monoalkyl ethers which have a carbon chain length of 6 to 22.

5. The composition according to claim 2, wherein the amphiphilic substance has a carbon chain length of 12 to 22.

6. The composition according to claim 2, wherein the physiologically acceptable salt of the tranexamate ester has a carbon chain length of 12 to 18, and the amphiphilic substance has a carbon chain length of 12 to 22.

7. The composition according to claim 1, wherein the physiologically acceptable salt of a tranexamate ester is cetyl tranexamate hydrochloride.

8. The composition according to claim 7, wherein the amphiphilic substance comprises at least one substance selected from a group consisting of alcohols, fatty acids, fatty acid esters, fatty acid ethers, glycerin fatty acid esters and glycerin monoalkyl ethers which have a carbon chain length of 6 to 22.

9. The composition according to claim 7, wherein the amphiphilic substance has a carbon chain length of 12 to 22.

10. The composition according to claim 7, wherein the physiologically acceptable salt of the tranexamate ester has a carbon chain length of 12 to 18, and the amphiphilic substance has a carbon chain length of 12 to 22.

11. The composition according to claim 1, wherein the amphiphilic substance comprises at least one substance selected from a group consisting of alcohols, fatty acids, fatty acid esters, fatty acid ethers, glycerin fatty acid esters and glycerin monoalkyl ethers which have a carbon chain length of 6 to 22.

12. The composition according to claim 11, wherein the amphiphilic substance has a carbon chain length of 12 to 22.

13. The composition according to claim 1, wherein the amphiphilic substance has a carbon chain length of 12 to 22.

14. The composition according to claim 1, wherein the physiologically acceptable salt of the tranexamate ester has a carbon chain length of 12 to 18, and the amphiphilic substance has a carbon chain length of 12 to 22.

15. A method for producing an oil-in-water emulsion composition, comprising the steps of:
preparing an oil phase comprising:
A) a physiologically acceptable salt of a tranexamate ester,
B) an amphiphilic substance,
C) an oily substance and
D) water, a water-soluble organic solvent or a mixture thereof,
wherein a weight ratio of the ingredients A:B is in the range of 1:1 to 1:2, a weight ratio of the ingredients A:C is in the range of 1:1 to 1:5.0, and a weight ratio of the ingredients A:D is 1:0.2 to 1:5.0; and adding the oil phase to an aqueous phase comprising E) water, a water-soluble organic solvent or a mixture thereof.

16. The method according to claim 15, wherein the weight ratio of oil phase: aqueous phase is in the range of 1:1 to 30.

17. The method according to claim 15, wherein the oil phase and the aqueous phase are respectively heated to a temperature within a range of 75° C. to 95° C. and dissolved, before adding said oil phase to said aqueous phase.

18. A cosmetic method for inhibiting skin pigmentation and/or for whitening the skin, the method comprising topical application to the skin of the composition according to claim 1.

\* \* \* \* \*